US00PP10465P

United States Patent [19]

Wain

[11] Patent Number: Plant 10,465

[45] Date of Patent: Jun. 23, 1998

[54] CHRYSANTHEMUM PLANT NAMED 'CLEAGAR NG1'

[75] Inventor: Peter Wain, Portsmouth, United Kingdom

[73] Assignee: Cleangro Limited, United Kingdom

[21] Appl. No.: 751,863

[22] Filed: Nov. 18, 1996

[51] Int. Cl.[6] ..... A01H 5/00

[52] U.S. Cl. ..... Plt./82

[58] Field of Search ..... Plt./76, 82

[56] References Cited

U.S. PATENT DOCUMENTS

P.P. 4,884 9/1982 Jessel, Jr. et al. ..... Plt./78

OTHER PUBLICATIONS

Sunnyslope Gardens, "Chrysanthemums 1992", p. 7, 1992.

Sunnyslope Gardens, "'83 Chrysanthemums", p. 12, 1983.

*Primary Examiner*—Howard J. Locker

*Attorney, Agent, or Firm*—Christie, Parker & Hale L.L.P.

[57] ABSTRACT

A distinct cultivar of Chrysanthemum plant named ('Cleagar ng1'), characterized by its uniform plant habit, vigorous and upright growth habit; pompon inflorescences; bi-colored inflorescence appearance with red bronze adaxial ray floret surfaces and pale gold abaxial ray floret surfaces; small, but numerous inflorescences per plant; numerous ray florets per inflorescence; and good garden performance.

2 Drawing Sheets

The present invention relates to a new and distinct cultivar of garden Chrysanthemum plant, botanically known as *Dendranthema grandiflora* and referred to by the cultivar name 'Cleagar ng1'.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the commercial cultivar 'Bravo' (U.S. Plant Pat. No. 6,888) as the female, or seed, parent with the proprietary selection 10/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Cleagar ng1'. These characteristics in combination distinguish 'Cleagar ng1' as a new and distinct cultivar:

1. Uniform plant habit, vigorous and upright growth habit.
2. Pompon inflorescences.
3. Bi-colored inflorescence appearance with red bronze adaxial ray floret surfaces and pale gold abaxial ray floret surfaces.
4. Small, but numerous inflorescences per plant.
5. Numerous ray florets per inflorescence.
6. Good garden performance.

The cultivar 'Cleagar ng1' has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum are more upright, retain ray floret color longer and flower later than plants of the female parent, the cultivar 'Bravo'. In addition, plants of the new Chrysanthemum have smaller pompon inflorescences whereas plants of the cultivar 'Bravo' have larger decorative-type inflorescences. In the same comparisons, plants of the new Chrysanthemum are more upright, less dense, not as freely branching and flower earlier than plants of the male parent, the proprietary selection 10/GM/94. In addition, plants of the new Chrysanthemum have red bronze pompon inflorescences whereas plants of the proprietary selection 10/GM/94 have yellow daisy-type inflorscences.

Plants of the new Chrysanthemum can be compared to the cultivar Dark Grenadine (U.S. Plant Pat. No. 7,632). However, in side-by-side comparisons conducted in Oxnard, Calif., under commercial practice, plants of the new Chrysanthemum differed from plants of the cultivar 'Dark Grenadine' in the following characteristics:

1. Plants of the new Chrysanthemum are denser, more uniform and more vigorous than plants of the cultivar 'Dark Grenadine'.
2. Plants of the new Chrysanthemum have pompon inflorescences whereas plants of the cultivar 'Dark Grenadine' have decorative-type inflorescences.
3. Plants of the new Chrysanthemum have smaller inflorescences but more inflorescences per flowering stem than plants of the cultiavar 'Dark Grenadine'.
4. Ray florets of plants of the new Chrysanthemum have a more striking bi-color appearance with darker red-bronze adaxial surface color and more intense gold abaxial surface color compared to plants of the cultivar 'Dark Grenadine'.
5. Plants of the new Chrysanthemum have more upright, longer and stronger peduncles than plants of the cultivar 'Dark Grenadine'.

A detailed comparison of plants of the new Chrysanthemum and the cultivar 'Dark Grenadine' appears in Chart A at the end of the specification.

The accompanying colored photographs illustrate the overall appearance of the cultivar, showing the colors as true as it is reasonably possible to obtain in colored reproduction of this type.

The first photograph comprises a side perspective view of a typical flowering 16.5-cm container of 'Cleagar ng1' with one cutting in the container.

The second photograph comprises a close-up view of five leaves at different stages of development and a fully opened inflorescence.

Foliage and floret colors in the photographs may appear different from the actual colors due to light reflectance.

In the following description, color reference are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 30C, and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar 'Cleagar ng1'.

Commercial classification: Garden Chrysanthemum.

Parentage:

*Female, or seed, parent.*—*Dendranthema grandiflora* commercial cultivar 'Bravo' (U.S. Plant Pat. No. 6,888).

*Male, or pollen, parent.*—*Dendranthema grandiflora* proprietary selection 10/GM/94.

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Uniform in plant habit, vigorous and medium in height, stems upright.

*Plant height.*—About 25 cm.

*Lateral branch length.*—About 20 cm.

*Quantity of lateral branches after removal of apical meristem.*—Usually 3 to 4.

*Stem color.*—147C.

*Foliage description.*—Number of leaves per plant: About 50. Number of leaves per lateral branch: About 12. Leaf arrangement: Alternate. Leaf size, fully expanded: Length: About 5 cm. Width: About 3.6 cm. Leaf apex: Rounded apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.2 cm. Color: Young foliage adaxial surface: 147A. Young foliage abaxial surface: 147B. Fully expanded foliage adaxial surface: 147A. Fully expanded foliage abaxial surface: 147B. Venation adaxial surface: 147C. Venation abaxial surface: 147B. Petiole: 147C.

Inflorescence description:

*Appearance.*—Pompon inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 to 4 weeks of long day/short night conditions after sticking followed by photoinductive short day/long night conditions, flower about 49 days later.

*Quantity of inflorescences.*—About 8 inflorescences per flowering stem.

*Inflorescence size.*—Diameter: About 3 cm. Depth (height): About 1.4 cm. Diameter of disc: About 2 mm.

*Opening inflorscences.*—Bud shape: Spherical. Bud size: Length: About 7 mm. Width: About 9 mm. Bud color: 185A.

*Ray florets.*—Shape: Cordate, short tube at proximal end with spoon tip. Size: Length: About 1.2 cm. Width: About 4.5 mm. Apex: Tri- or quad-dentate with one deep notch. Base: Acute. Margin: Entire. Texture: Smooth, matte and glabrous. Aspect: Slightly erect. Number of ray florets per inflorescence: About 145. Color: When opening, adaxial surface: 179A. When opening, abaxial surface: 161B. Mature, adaxial surface: 181B. Mature, abaxial surface: 161B. Fading to: 181C.

*Disc florets.*—Shape: Tubular. Size: Length: About 3 mm. Width: About 1 mm. Number of disc florets per inflorescence: About 5. Color: Immature: 154D. Mature: 154D.

*Peduncle.*—Aspect: Strong and angled 30° to 40° to the stem. Length: First peduncle: About 4.6 cm. Fourth peduncle: About 8.2 cm. Texture: Pubescent. Color: 147C.

*Reproductive organs.*—Androecium: Present on disc florets only. Anther color: 12A. Pollen: Moderate, 12A in color. Gynoecium: Present on both ray and disc florets. Style color: 154C.

Disease resistance: Under commercial greenhouse and garden conditions, plants of the new Chrysanthemum have not demonstrated resistance, tolerance nor susceptibility to diseases common to Chrysanthemums.

Seed production: Seed production has not been observed.

CHART A

| CHARACTERISTIC | CLEAGAR NG1 | 'DARK GRENADINE' |
|---|---|---|
| PLANT SHAPE | Upright | Upright, rangy |
| GROWTH HABIT | Medium | Medium to tall |
| GROWTH RATE | Vigorous | Moderate |
| QUANTITY OF LEAVES PER LATERAL BRANCH | About 12 | About 13 |
| LEAF LENGTH | About 5 cm | About 4.6 cm |
| LEAF WIDTH | About 3.6 cm | About 4 cm |
| PETIOLE LENGTH | About 2.2 cm | About 1.9 cm |
| QUANTITY OF INFLORESCENSES PER LATERAL STEM | About 8 | About 5 |
| INFLORESCENCE DIAMETER | About 3 cm | About 5.2 cm |
| INFLORESCENCE DEPTH | About 1.4 cm | About 1.8 cm |
| BUD COLOR | 185A | 48B |
| RAY FLORET APPEARANCE/ASPECT | Short tube and spoon-tipped, slightly erect | Flat |
| RAY FLORET SHAPE | Cordate | Spatulate |
| RAY FLORET APEX | Tri- or quad-dentate with one deep notch | Mostly rounded with minute indentations |
| RAY FLORET LENGTH | About 1.2 cm | About 2.5 cm |
| RAY FLORET WIDTH | About 4.5 mm | About 8 mm |
| RAY FLORET COLOR, WHEN OPENING, ADAXIAL | 179A | 180B |
| RAY FLORET COLOR, WHEN OPENING, ABAXIAL | 161B | 24D |
| RAY FLORET COLOR, MATURE, ADAXIAL | 181B | 42D |
| RAY FLORET COLOR, | 161B | 23D |

-continued

CHART A

| CHARACTERISTIC | CLEAGAR NG1 | 'DARK GRENADINE' |
|---|---|---|
| MATURE, ABAXIAL RAY FLORET COLOR FADING TO | 181C | 37A |
| NUMBER OF RAY FLORETS PER INFLORESCENCE | About 145 | About 195 |
| DISC FLORET COLOR, IMMATURE | 154D | 1D |
| DISC FLORET COLOR, MATURE | 154D | 1D |
| PEDUNCLE LENGTH, FIRST | About 4.6 cm | About 3.8 cm |
| PEDUNCLE LENGTH, FOURTH | About 8.2 cm | About 5.5 cm |

-continued

CHART A

| CHARACTERISTIC | CLEAGAR NG1 | 'DARK GRENADINE' |
|---|---|---|
| PEDUNCLE STRENGTH | Strong | Moderate to weak |
| PEDUNCLE ANGLE TO STEM | 30 to 40° | About 40° |
| PEDUNCLE COLOR | 147C | 146D |
| ANTHER COLOR | 12A | 14B |
| POLLEN COLOR | 12A | 14B |

It is claimed:

1. A new and distinct cultivar of Chrysanthemum plant named 'Cleagar ng1', as illustrated and described.

* * * * *

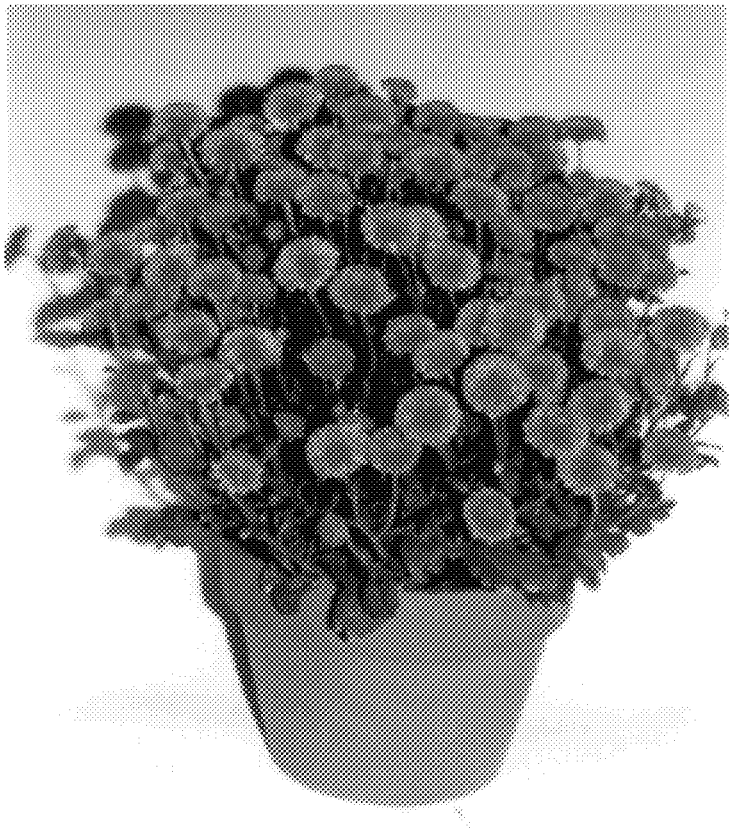

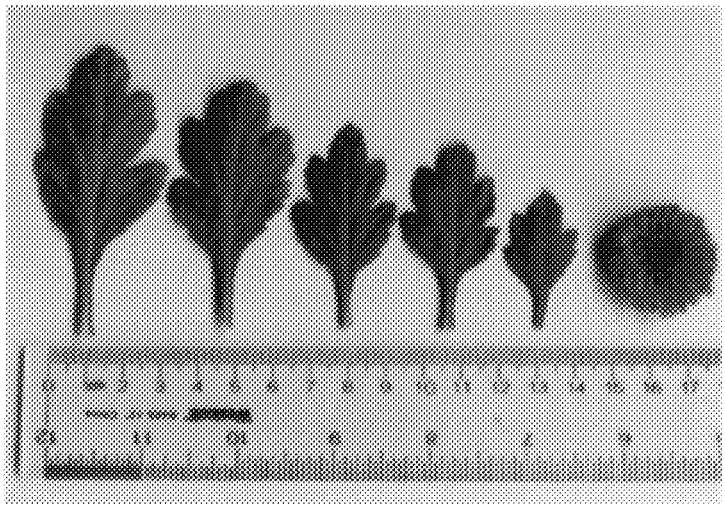

UNITED STATES PATENT AND TRADEMARK OFFICE

CERTIFICATE OF CORRECTION

PATENT NO. : PP 10,465

DATED : June 23, 1998

INVENTOR(S) : Peter Wain

It is certified that error appears in the above-indentified patent and that said Letters Patent is hereby corrected as shown below:

Column 2, line 10, change "inflorscences" to -- inflorescences --.
Column 2, line 24, change "cultiavar" to -- cultivar --.
Column 2, line 35, page 4, line 4, after "appearance of the" insert -- new --.
Column 3, line 3, change "reference" to -- references --.
Column 3, line 9, change "18C" to -- 18°C --.
Column 3, line 9, change "30C" to -- 30°C --.
Column 3, line 30, change "20C" to -- 20° C --.
Column 4, line 6, change "inflorscences" to -- inflorescences --.

Signed and Sealed this

Twelfth Day of October, 1999

*Attest:*

Q. TODD DICKINSON

*Attesting Officer*

*Acting Commissioner of Patents and Trademarks*